(12) United States Patent
Cho et al.

(10) Patent No.: US 11,430,140 B2
(45) Date of Patent: Aug. 30, 2022

(54) MEDICAL IMAGE GENERATION, LOCALIZATON, REGISTRATION SYSTEM

(71) Applicant: Caide Systems, Inc., Lowell, MA (US)

(72) Inventors: Jung Hwan Cho, Dracut, MA (US); Manohar Karki, North Billerica, MA (US); Kye Wook Lee, Groton, MA (US)

(73) Assignee: Caide Systems, Inc.

( * ) Notice: Subject to any disclaimer, the term of this patent is extended or adjusted under 35 U.S.C. 154(b) by 120 days.

(21) Appl. No.: 16/574,603

(22) Filed: Sep. 18, 2019

(65) Prior Publication Data
US 2020/0090350 A1     Mar. 19, 2020

Related U.S. Application Data

(60) Provisional application No. 62/732,733, filed on Sep. 18, 2018.

(51) Int. Cl.
*G06T 7/33*     (2017.01)
*G06T 7/136*    (2017.01)
(Continued)

(52) U.S. Cl.
CPC ............ *G06T 7/33* (2017.01); *G06N 3/0454* (2013.01); *G06T 3/0075* (2013.01); *G06T 7/0014* (2013.01); *G06T 7/136* (2017.01); *G16H 30/40* (2018.01); *G16H 50/70* (2018.01); *G06T 2207/10081* (2013.01); *G06T 2207/10088* (2013.01); *G06T 2207/20081* (2013.01); *G06T 2207/30016* (2013.01);
(Continued)

(58) Field of Classification Search
CPC ......... G06T 7/33; G06T 7/136; G06T 7/0014; G06T 3/0075; G06T 2207/30061; G06T 2207/30016; G06T 2207/30096; G06T 2207/10081; G06T 2207/10088; G06T 2207/20081; G06T 2207/20084; G06T 7/0012; G16H 50/70; G16H 30/40; G16H 10/60; G16H 50/20; G16H 30/20; G06N 3/0454; G06N 3/0472; G06N 3/088
USPC ....................................................... 382/128
See application file for complete search history.

(56) References Cited

U.S. PATENT DOCUMENTS 9,892,361 B2 *    2/2018  Nguyen ................... A61B 5/00
2013/0243244 A1 * 9/2013  Miyamoto ............ G06T 7/0014
                                                                  382/103
(Continued)

OTHER PUBLICATIONS

Tajbakhsh et al., "Convolutional neural networks for medical image analysis: Full training or fine tuning?," IEEE transactions on medical imaging 35:1299-1312, 2016,.
(Continued)

*Primary Examiner* — Amandeep Saini
(74) *Attorney, Agent, or Firm* — Occhiuti & Rohlicek LLP (57) ABSTRACT

A method for generating a synthesized medical image by receiving a normal image includes generating first data based on a random selection, generating second data, and, based at least in part on the first and second data, modifying the normal image to form the synthesized medical image. Modifying the normal image comprises combining the first data and the second data. The first data characterizes an image that represents a lesion and the second data characterizes a transformation of that image as well as a location of the lesion.

18 Claims, 10 Drawing Sheets

(51) Int. Cl.
    *G06T 7/00* (2017.01)
    *G06T 3/00* (2006.01)
    *G06N 3/04* (2006.01)
    *G16H 50/70* (2018.01)
    *G16H 30/40* (2018.01)
    *G16H 10/60* (2018.01)
    *G16H 50/20* (2018.01)

(52) U.S. Cl.
    CPC .............. *G06T 2207/30061* (2013.01); *G06T 2207/30096* (2013.01); *G16H 10/60* (2018.01); *G16H 50/20* (2018.01)

(56) References Cited

U.S. PATENT DOCUMENTS

| | | | | |
|---|---|---|---|---|
| 2014/0314295 | A1* | 10/2014 | Omi | G06V 10/7515 382/131 |
| 2017/0345149 | A1* | 11/2017 | Warntjes | A61B 5/0042 |
| 2019/0163949 | A1* | 5/2019 | Park | G06N 3/0445 |

OTHER PUBLICATIONS

Szegedy et al., "Going deeper with convolutions," Proc. Proceedings of the IEEE conference on computer vision and pattern recognition, 2014.

Krizhevsky et al., "Imagenet classification with deep convolutional neural networks." Proc. Advances in neural information processing systems.

Hua et al., "Computer-aided classification of lung nodules on computed tomography images via deep learning technique." OncoTargets and Therapy, 2015:8 pp. 2015-2022.

Hoo-Chang et al., "Deep convolutional neural networks for computer-aided detection: CNN architectures, dataset characteristics and transfer learning," IEEE transactions on medical imaging 35:1285, 2016.

Schlegl et al., "Unsupervised pre-training across image domains improves lung tissue classification," Proc. International MICCAI Workshop on Medical Computer Vision, MCV 2014.

Margeta et al.,"Fine-tuned convolutional neural nets for cardiac MRI acquisition plane recognition," Computer Methods in Biomechanics and Biomedical Engineering: Imaging & Visualization 5:339-349, 2017.

Van Ginneken et al., "Off-the-shelf convolutional neural network features for pulmonary nodule detection in computed tomography scans," Proc. Biomedical Imaging (ISBI), 2015 IEEE 12th International Symposium.

Simard et al., "Best practices for convolutional neural networks applied to visual document analysis," Proc. of the Seventh Intl. Conf. on Document Analysis and Recogittion (ICDAR 2003) IEEE.

Chatfield et al., "Return of the devil in the details: Delving deep into convolutional nets," arXiv preprint arXiv:14053531, 2014.

Sapp et al., "A Fast Data Collection and Augmentation Procedure for Object Recognition," Proc. of the Twenty-Third AAAI Conf. on Artificial Intelligence, 2008.

Goodfellow et al., "Generative Adversarial Nets," Proc. Advances in neural information processing systems, Departement d'informatique et de recherche operationnelle, Universite de Montreal, Montreal, QC.

Bao et al., "CVAE-GAN: Fine-grained image generation through asymmetric training," CoRR, abs/170310155 5, 2017.

Reed et al., "Generative adversarial text to image synthesis," University of Michigan, Ann Arbor, MI; Jun. 5, 2016.

Chuquicusma MJ, Hussein S, Burt J, Bagci U: "How to fool radiologists with generative adversarial networks? A visual turing test for lung cancer diagnosis." Proc. Biomedical Imaging (ISBI 2018), IEEE 15th International Symposium on Biomedical Imaging, 2018.

Costa et al., "End-to-end adversarial retinal image synthesis," IEEE Transactions on Medical Imaging, 37:3 pp. 781-791, 2018.

Zhao et al., "Synthesizing retinal and neuronal images with generative adversarial nets," Medical Image Analysis, 49:14-26, 2018.

Hou et al., "Unsupervised Histopathology Image Synthesis," arXiv: 1712.05021v1 [cs.CV] Dec. 13, 2017.

Baur et al., "MelanoGANs: High Resolution Skin Lesion Synthesis with GANs," arXiv:1804.04338v1 [cs.CV] Apr. 12, 2018.

Bi et al., "Synthesis of positron emission tomography (pet) images via multi-channel generative adversarial networks (GANS)," arXiv:1707.09747v1 [cs CV] 2017.

Ben-Cohen et al., "Virtual PET Images from CT data using deep convolutional networks: Initial results," Proc. International Workshop on Simulation and Synthesis in Medical Imaging, 2017.

Wolterink et al., "Deep MR to CT Synthesis using Unpaired Data," Proc. International Workshop on Simulation and Synthesis in Medical Imaging, 2017.

Nie et al., "Medical Image Synthesis with Deep Convolutional Adversarial Networks," IEEE Trans. on Biomedical Engineering, 65:12 pp. 2720-2730, 2018.

Rorden et al., "Age-specific CT and MRI templates for spatial normalization," *NeuroImage* 61:957-965, 2012.

Fillmore et al., "Age-specific MRI brain and head templates for healthy adults from 20 through 89 years of age," Front. Aging Neurosci. 7:44, doi: 10.3389/fnagi.2015.00044.

De Vos et al., "End-to-end unsupervised deformable image registration with a convolutional neural network," Springer, arXiv:1704.06065v1 [cs.CV] 2017.

Balakrishnan et al., "An Unsupervised Learning Model for Deformable Medical Image Registration," Proc. Proceedings of the IEEE Conference on Computer Vision and Pattern Recognition, arXiv:1802.02604v3 [cs.CV] 2018.

Jaderberg et al., "Spatial Transformer Networks," Proc. Advances in neural information processing systems, arXiv:1506.02025v3 [cs.CV] 2016.

Simonyan K, Zisserman AJapa, "Very deep convolutional networks for large-scale image recognition," Published as Conference Paper at ICLR, arXiv:1409.1556v6 [cs.CV] 2015.

Szegedy et al., "Rethinking the inception architecture for computer vision," Proc. Proceedings of the IEEE conference on computer vision and pattern recognition, arXiv:1512.00567v3 [cs.CV] 2015.

He et al., "Deep residual learning for image recognition," Proc. Proceedings of the IEEE conference on computer vision and pattern recognition, http://imagenet.org/challenges/LSVRC/2015/ and http://mscoco.org/dataset/#detections-challenge2015.

\* cited by examiner

MEDICAL IMAGE GENERATION, LOCALIZATON, REGISTRATION SYSTEM

RELATED APPLICATIONS

This application claims the benefit of the Sep. 18, 2018 priority date of U.S. Provisional Application 62/732,733, the contents of which are herein incorporated by reference.

FIELD OF INVENTION

The invention relates to medical imaging and in particular to methods and systems for facilitating the analysis of medical images.

BACKGROUND

A variety of ways exist to non-invasively obtain medical images. These include magnetic resonance imaging and computerized tomography.

Using such images, it is possible to identify lesions in various places that would otherwise be difficult to inspect directly. In particular, such methods can be used to inspect the brain.

In the course of inspecting an image of the brain, one sometimes finds lesions. The significance of such lesions varies as a function of morphology and location. Thus, it is useful to accurately characterize these lesions to promote more accurate diagnosis.

Although non-invasive imaging is a useful way to detect lesions in the brain, it is somewhat difficult to accurately characterize these lesions. Known methods of doing so are tedious and error-prone.

SUMMARY

The subject matter described and claimed herein relies on the augmentation of data to permit the generation of more realistic and diverse images. It also relies creation of a template and an atlas for automatic lesion ground-truth construction by creating a template and atlas.

The data-augmentation procedure relies on a generative deep-learning model that uses a semi-synthetic image generation. These semi-synthetic images are generated through combination of a real image and synthetic lesion images with localization. As a result, it is only necessary to generate the lesion. It is not necessary to generate the remainder of the image. This means that resources can be focused on localization and synthesis of only the lesions.

The method uses a real image and a generated image. The real image, which is used as a background, is obtained by scanning healthy patients using computerized tomography or magnetic-resonance imaging. The generated images are lesion-segmented images that come from generative adversarial networks. These networks have been trained using data from patients that exhibit certain abnormalities. Examples of such abnormalities include hemorrhages and brain tumors.

By gathering the normal images from a large and diverse population group, it is possible to form intersections of these normal images to target a variety of demographic constraints. In one practice, the normal images span a three-dimensional space whose basis is defined by age, sex, and race or ethnicity. This makes it possible to obtain background images that are more finely tuned to a particular patient. As a result, the background image can be made quite realistic, with only the lesion having to be filled in to complete the image. The image of this lesion can be localized by spatial transformer networks. A discriminator implemented by a convolutional neural network provides an objective basis for judging whether the final lesion-filled image is real or not.

The image-generation process relies on a template-based ground-truth annotation method to promote the ability to automatically find multiple abnormalities, to segment the lesions associated with these abnormalities, and to then label them according to both their location and their morphology. To avoid complications that result from the diversity associated with anatomical structures of different individuals, the method also includes the use of customized deep convolution networks to normalize images to any one of a variety of standard templates that exist for computerized tomography images and magnetic resonance images.

The process for automatically detecting an abnormality in an image relies on three steps.

A first step includes reshaping individual anatomical images to match the size and shape of a template image. This step relies on an encoder and decoder based deep convolutional architecture that carries out a non-linear mapping from an individual anatomical structure to a standard template. The resulting image is a "normalized image."

A second step is that of comparing the normalized image to a normal image. This comparison relies on a voxel-wise outlier detection approach based on Crawford-Howell t-test, the result of which is a probability map based on the t-test score.

The third and final step is that of transforming the lesion-overlaid image out of the space defined by the standard template and back to the original space.

In one aspect, the invention features a method for generating a synthesized medical image by receiving a normal image, generating first data based on a random selection, generating second data, and, based at least in part on the first and second data, modifying the normal image to form the synthesized medical image. In this method, modifying the normal image comprises combining the first data and the second data. The first data characterizes an image that represents a lesion and the second data characterizes a transformation of that image as well as a location of the lesion.

Practices of the invention include those in which generating the first data comprises generating a base lesion image. In such practices, the second data represents a sampling of the base lesion image for forming the transformation. Among the foregoing practices are those in which modifying the normal image comprises combining image values and locations of the normal image with corresponding image values from the transformation of the image.

Yet other practices include generating the first data and the second data by applying at least one computer-implemented non-linear transformation to a randomly-generated quantity. This non-linear transformation is parameterized by first parameters. Among these practices are those that also include using a computer-implemented training controller to determine values for the first parameters and values for second parameters of a parametrized discriminator that distinguishes between synthesized images and real lesion-containing images. This is followed by a step of providing real lesion-containing images and synthesized images to the parameterized discriminator, selecting values of the first parameters to reduce an aggregate measure of discriminability between real lesion-containing images and synthesized images, and selecting values of the second parameters that increase the discriminability. In these practices, the second parameters are parameters of a parameterized discriminator for distinguishing synthesized images and real lesion-containing images.

Also among the practices are those in which the lesion is a brain lesion and those in which the lesion is a lung lesion.

In some practices of the method, modifying the normal image to form the synthesized medical image includes directly altering image values of the normal image to synthesize an altered normal-image. Among these are those practices that also include reducing an aggregate measure of discriminability between the altered normal-image and real lesion-containing images.

The methods and systems described herein circumvent the tedium of annotating images to delineate target lesions and avoid the difficulty associated with having to obtain copious amounts of imaging data for training of a deep convolutional neural network. Additionally, these methods and systems promote consistency in annotated ground truth labels that arises in part from reliance on the inherently subjective nature of data labeled by different humans who will inevitably make different judgment calls.

All methods and systems described herein are of the non-abstract variety. As such, all claims presented herein recite non-abstract subject matter and only non-abstract subject matter. Any person who construes the claims as covering abstract subject matter would therefore have done so incorrectly and, in doing so, would have failed to construe the claims in light of the specification as required by law. Applicant, acting as his own lexicographer, hereby defines "non-abstract" as describing subject matter that is covered by 35 USC 101 as of the filing date of this application.

These and other features of the invention will be apparent from the following detailed description and its accompanying figures, in which:

DETAILED DESCRIPTION

Figure 1:
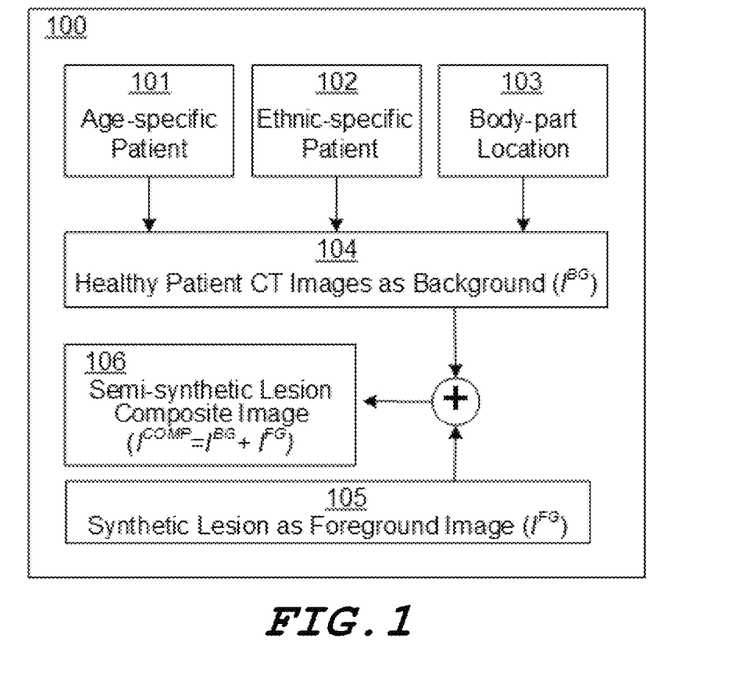
FIG. 1 is a block diagram of an embodiment of a semi-synthetic lesion composite image generation and localization system.

FIG. 1 shows a system 100 that semi-synthetically generates and localizes a composite lesion image 106 based on two images: a background 104 and a foreground 105.

The background 104 is derived from actual images that have been acquired from healthy patients. These images are typically acquired by computerized tomography and/or magnetic-resonance imaging. In the particular example shown in FIG. 1, the actual images have been organized to conform to first, second, and third sets 101, 102, 103. This enables one to pick and choose actual images to generate a suitable background 104 for a particular application.

In the illustrated embodiment, the first set 101 comprises images that have been classified based on the patient's age, the second set 102 comprises images that have been classified based on the patient's ethnicity, and the third set 103 comprises images that have been classified based on the anatomical feature that was imaged. Thus, based on taking appropriate intersections of these sets, it is possible to assemble a background 104 representative of a particular demographic group. For example, one could obtain brain CT images from healthy twenty-year-old Korean patients using an appropriate intersection of the first, second, and third sets 101, 102, 103.

The particular sets 101, 102, 103 shown in FIG. 1 are useful for many applications. However, they do not represent the only possible ways to define sets. For example, one can imagine sets defined based on gender, such as male, female, and combinations thereof, or lifestyle, such as smokers and non-smokers or vegetarians and omnivores.

The foreground 105 comes from images of lesions synthesized from a lesion processor 200. These images are likewise synthetically generated either by computerized tomography or by magnetic resonance imaging.

The resulting composite lesion image 106 is considered semi-synthetic because it is a combination of the background 104 and the foreground 105. Thus, the resulting composite lesion image 106 is a combination of a synthetic and non-synthetic component.

Figure 2:
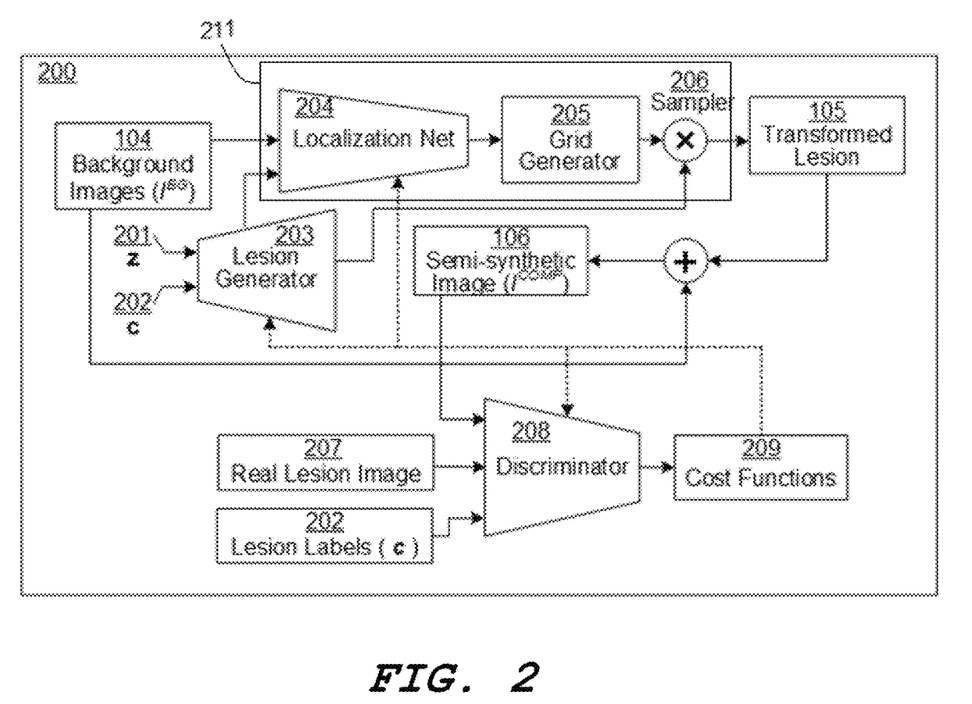
FIG. 2 is a block diagram of an embodiment of a lesion processor.

Referring now to FIG. 2, a lesion processor 200 for semi-synthetic generation of the composite lesion image 106 includes a lesion generator 203 and a lesion localizer 211, both of which are to be trained based on the foreground 105. In the particular embodiment described herein, the lesion generator 203 and the lesion localizer 211 are both trained using an unsupervised learning method.

The lesion generator 203 constructs a generative adversarial network based on two inputs: a noise vector 201 and a label vector 202. These are labelled as "z" and "c" in FIG. 2.

The noise vector 201 represents gaussian random noise. The label vector 202 is a conditional label vector that contains lesion labels. In some embodiments, the label vector 202 includes labels for one or more of hemorrhagic lesions, including labels for an intraparenchymal hemorrhage (IPH), an intraventricular hemorrhage (IVH), an extradural hemorrhage (EDH), a subdural hemorrhage (SDH), and a subarachnoid hemorrhage (SAH).

The lesion generator 203 uses the noise vector 201 to produce a fake lesion that appears realistic. It does so by mapping the noise vector 201 into a lesion image through a series of transposed convolutions. In a typical embodiment, the lesion generator 203 maps a 100-dimensional noise vector into a 512×512 lesion image.

The lesion localizer 211 relies on a spatial-transformer network that includes a localization network 204, a grid generator 205, and a sampler 206.

The localization network 204 is a non-linear function mapping that accepts two conditional input feature maps: a lesion image provided by the lesion generator 203 and the background 104. It then outputs a transformation parameter that allow a lesion to be rotated, translated, and scaled. In one embodiment, the transformation parameter is a six-dimensional vector of an affine transformation.

There exist a variety of implementations for the localization network 204. These implementations rely on either a convolutional neural network or fully-connected layers. It is, however, particularly advantageous to have a regression layer as the last layer of the network. Such a regression layer promotes the ability to predict transformation parameters that are to be provided to a grid generator 205.

The grid generator 205 receives the transformation parameters and uses them to create a parametrized sampling grid. This grid defines source coordinates.

A sampler 206 receives this grid, samples each source coordinate, and uses these samples to produce an output feature map. To do so, the sampler 206 executes an interpolator. Examples of suitable interpolators include a bilinear interpolator and a nearest-integer interpolator. The end result is a transformed lesion 105 that is to be combined with the background 104 to form the composite lesion image 106 shown in FIG. 1. The transformed lesion 105 thus corresponds to the foreground 105 in FIG. 1.

Figure 3:
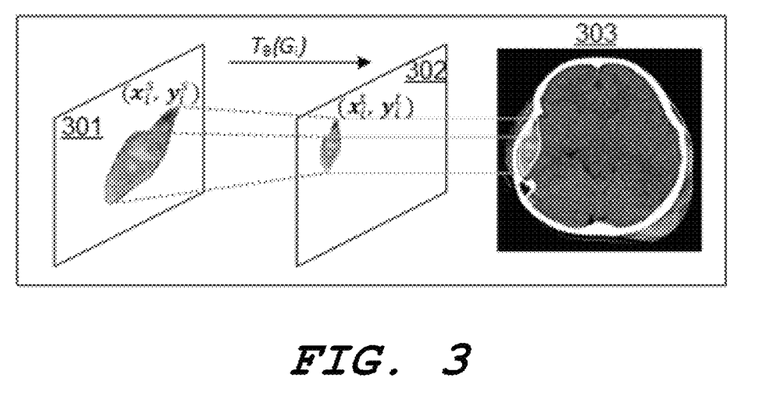
FIG. 3 illustrates an example of a hemorrhagic lesion localization using a spatial transformation network.

FIG. 3 shows an input feature map 301 having a set of samples $(x_i^s, y_i^s)$ such as those provided by the sampler 206. The process of generating the transformed lesion 105 includes carrying out a spatial transformation $T_\theta$ that maps these samples $(x_i^s, y_i^s)$ to corresponding target coordinates $(x_i^t, y_i^t)$ in an output feature map 302. This output feature map 302 is eventually relied upon to carry out an iteration that results in a final lesion-filled image 303.

The goal is for the final lesion-filled image 303 to be essentially indistinguishable from a real image. In an effort to achieve this goal, it is useful to train the lesion generator 203 and the lesion localizer 211 to learn how to choose the transformation parameter, and in particular the rotation, scale, and translation to be applied to a lesion, so as to create increasingly indistinguishable lesion-filled images 303.

Figure 4:
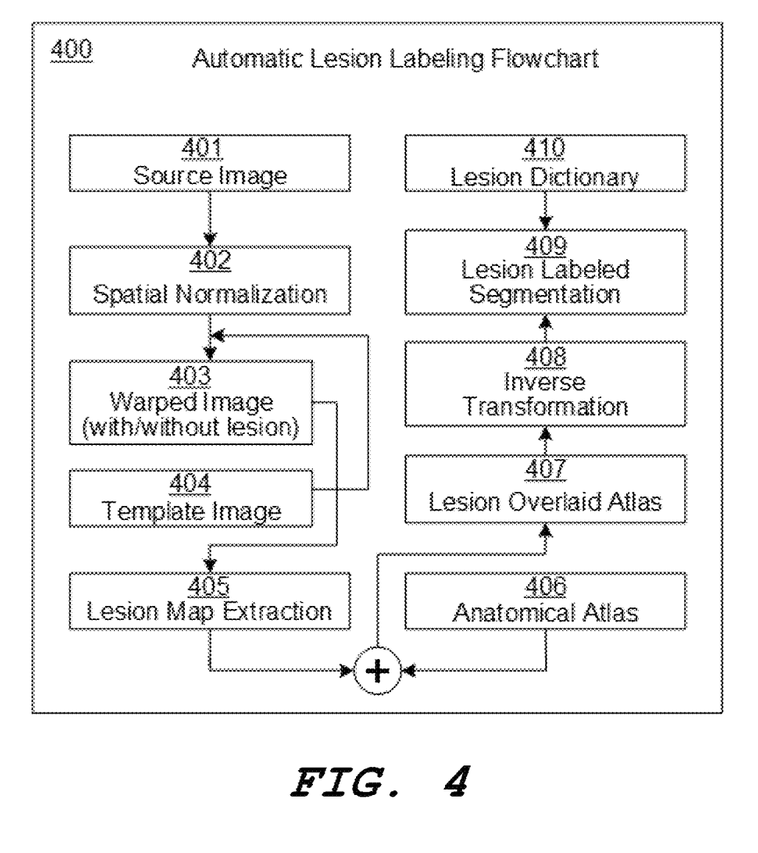
FIG. 4 is a flowchart of an automatic ground-truth extraction and lesion labeling procedure.
Figure 5:
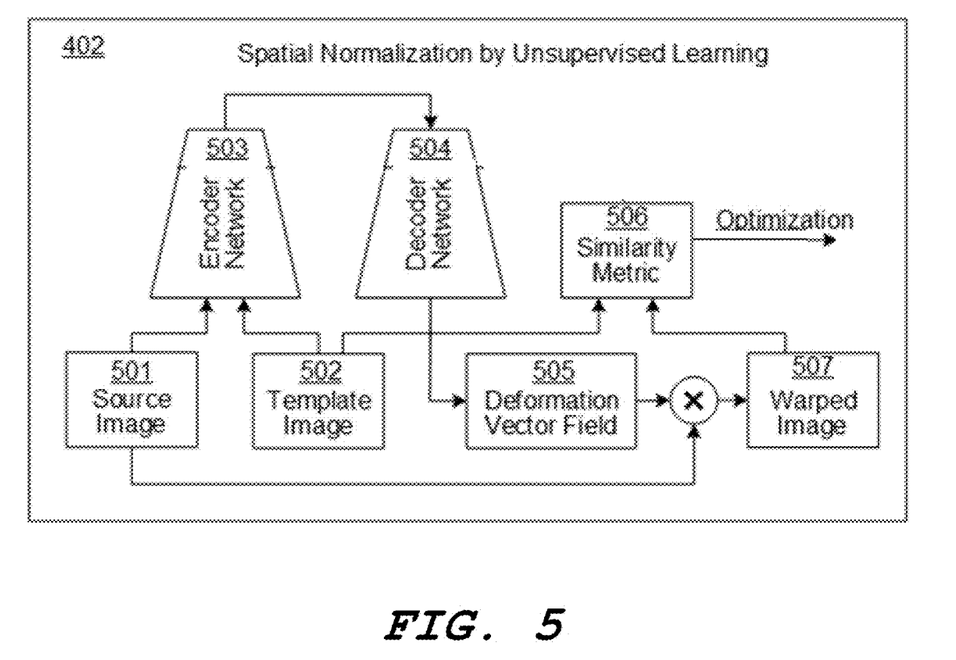
FIG. 5 illustrates an embodiment of a spatial normalization procedure that uses a spatial transformation network.
Figure 6:
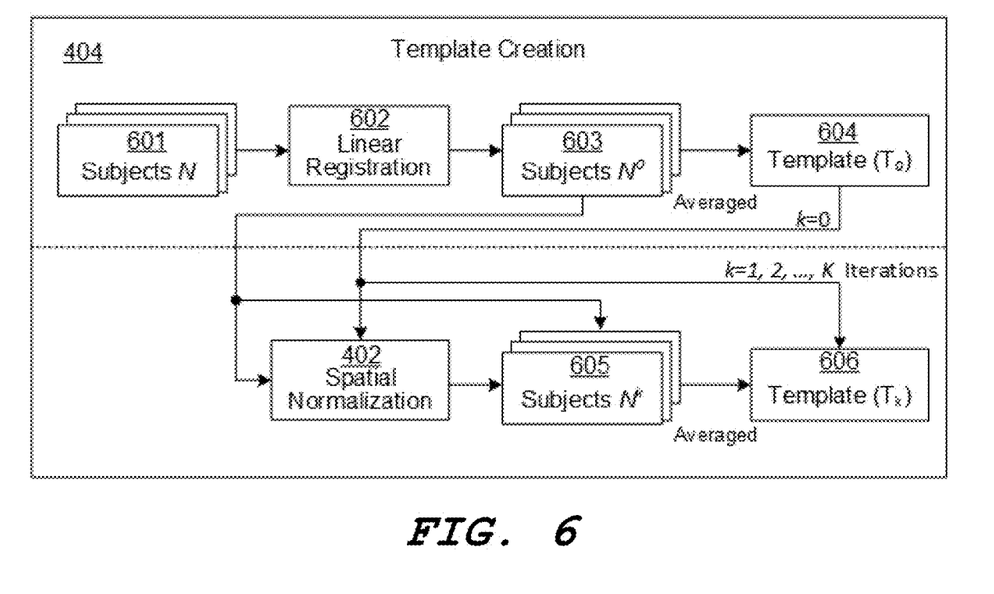
FIG. 6 illustrates an embodiment of a template creation procedure for spatial normalization.
Figure 7:
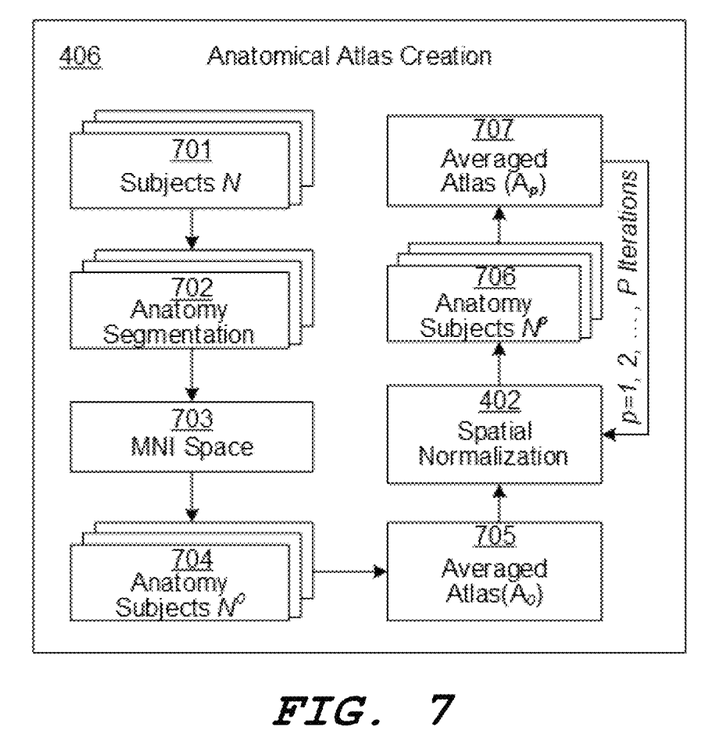
FIG. 7 is a flowchart diagram of an embodiment of an anatomical atlas creation procedure.

FIG. 4 shows a flowchart of an image-generating procedure 400 for automatically generating a lesion-labelled image. FIGS. 5, 6, and 7 illustrate three components of the image-generating procedure 400: a spatial normalization process 402, a template image 404, and an anatomical atlas 406.

The spatial normalization process 402 transforms a source image 401 into a template image 404. Images from both healthy patients without lesions, which serve as a control group, and patients with lesions are normalized into the template volume 404. By comparing the template image 403 with the warped image 403, the lesions are generated. Although different comparison procedures can be used, one that is particularly useful is a voxel-wise outlier detector based on a Crawford-Howell t-test. This results in a t-test score that can be used as a basis for lesion-map extraction 405, the result of which is an extracted lesion.

The anatomical atlas 406 represents an averaged segmented anatomy of N healthy populations. Overlaying the anatomical atlas 406 on the extracted lesions results in a lesion-overlaid atlas 407.

An inverse-transformation matrix 408 transforms this lesion-overlaid atlas 407 into an original coordinate space. This inverse-transformation matrix 408 will have been calculated as part of the spatial normalization process 402.

The image-generating procedure 400 relies on a lesion dictionary 410 for its final step. This lesion dictionary 410 provides lesion names and their anatomical locations. It comes from either Electronic Health Records (EHR) or from radiology reports. It also matches hyperdense or hypodense regions to the lesion segmented image. These locations are of particular significance in the case of certain kinds of brain lesions, such as those associated with an aneurysm, a tumor, hydrocephalus, stroke, traumatic brain injury, and the like. This is because the incidence of stroke may be associated with the existence of an intracranial hemorrhage on the left side of the brain's frontal lobe.

FIG. 5 shows details of the spatial normalization process 402 discussed in connection with FIG. 4 for registering a source image 501 with a template image 502. These would correspond to the source image 401 and template image 404 in FIG. 4. The spatial normalization process 402 achieves such registration by minimizing difference between the source image 501 and the template image 502.

The process of minimizing this difference relies on a deformation vector field 505 that is progressively refined as a result of training by an encoder network 503 and a decoder network 504.

To monitor the growing similarity that results from minimizing this difference, the spatial normalization process 402 features a similarity metric 506 that measures similarity based on cross-correlation between a warped image 507 and the template image 502.

A variety of ways exist for implementing the encoder network 503. In some embodiments, the encoder network 503 is a convolutional neural network that includes a standard form, an inception module, and a residual block.

The implementation of the encoder network 503 dictates that of the decoder network 504. In the illustrated embodiment, the decoder network 504 up-samples using either a deconvolution operator or a transposed convolution operator. As a result, the decoder network 504 produces a deformable vector field 505 that can be used to enable the source image 501 to register into the template image 502.

Although not required, it is possible to incorporate additional features into the decoder network 504 to generate an output with higher spatial resolution or final spatial scales, thus enabling more accurate registration with anatomical features. Examples of such additional features include skip connection or pyramid pooling.

FIG. 6 shows one implementation of a process for creating the template image 404 referred to in FIG. 4. The illustrated process relies on iterative refinement of templates beginning with a starting template and culminating in an output template that is ultimately used in the manner shown in connection with FIG. 4.

The process for creating an output template begins with creation of a standard template. This begins with collection of baseline image data 601 from N populations of healthy subjects. This image data comes from computerized tomography or magnetic resonance imaging. This baseline image data 601 is then provided to a linear registration module 602.

The linear registration module 602 carries out scaling, rotation, and affine transformation, thus normalizing the baseline image data 601 into a standard template. A suitable standard template is that specified by the Montreal Neurological Institute. This results in a set of initially warped images $N^0$ 603 that can then be averaged to construct an initial template 604. It is this initial template 604 that serves as the starting point for an iterative refinement that follows. This iterative refinement that eventually results in an output template.

The iterative refinement begins with performing spatial normalization process 402 using this initial template 604. Repeated execution of the spatial registration procedures results in a set of transformed subjects 605. Averaging these transformed subjects 605 then yields an output template 606.

Referring now to FIG. 7, the procedure for anatomical-atlas creation 406 mirrors that of template creation 404. The main difference between a template and an atlas is that a template provides a coordinate frame that represents the averaged N subjects. An atlas, on the other hand, summarizes the segmented data from the N individual subjects that are represented in the template's coordinate frame.

Referring to FIG. 7, anatomical-atlas creation 406 begins with acquisition of initial subject data 701. This subject data 701 is then segmented to yield segmented data 702. The segmentation is typically carried out manually. For example, the brain anatomy can be segmented into twenty-one regions, which including the frontal, parietal, and temporal lobes. The resulting segmented data is then transformed into a standard template 703. In the illustrated embodiments, the standard template 703 is that specified by the Montreal Neurological Institute ("MNI"). This results in a set of transformed subjects 704 that can then be averaged together to yield an averaged atlas 705 that serves as a starting point for iterative refinement.

The iterative refinement for creating an atlas includes carrying out spatial normalization process 402 on the averaged atlas 705 to generate a new averaged atlas 707, which can then be used as a starting point for another iteration of the spatial normalization process 402. These iterations continue until some user-specified termination condition has been met, at which point the anatomical atlas used in FIG. 4 will have been created.

Figure 8:
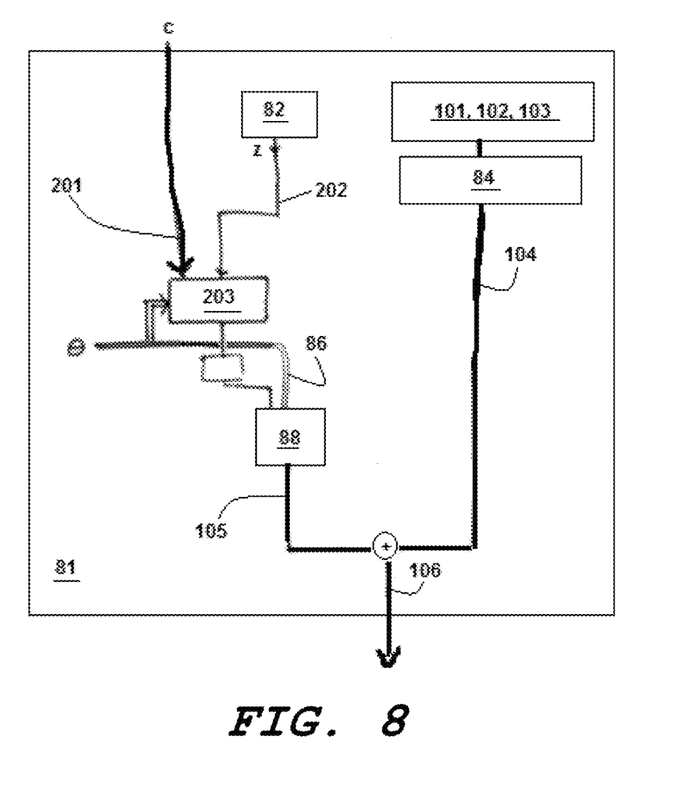
FIG. 8 shows a data flow representation of a runtime image generator.

FIG. 8 shows data flow associated with a runtime image generator 81 for the system 100. The runtime image generator 81 includes a random-vector generator 82 that generates the noise vector 202 and provides it to a lesion generator 203. The lesion generator 203 also receives the label vector 202. The lesion generator 203 uses these as a basis for generating a base lesion image 86, which is then provided to a lesion transformer 88 to generate the transformed lesion 105, which is ultimately the foreground 105 from FIG. 1. Meanwhile, a selector 84 selects an appropriate combination of the sets 101, 102, 103 of actual images to form the background 104. The background 104 and foreground 105 are then combined to form the composite lesion image 106.

Figure 9:
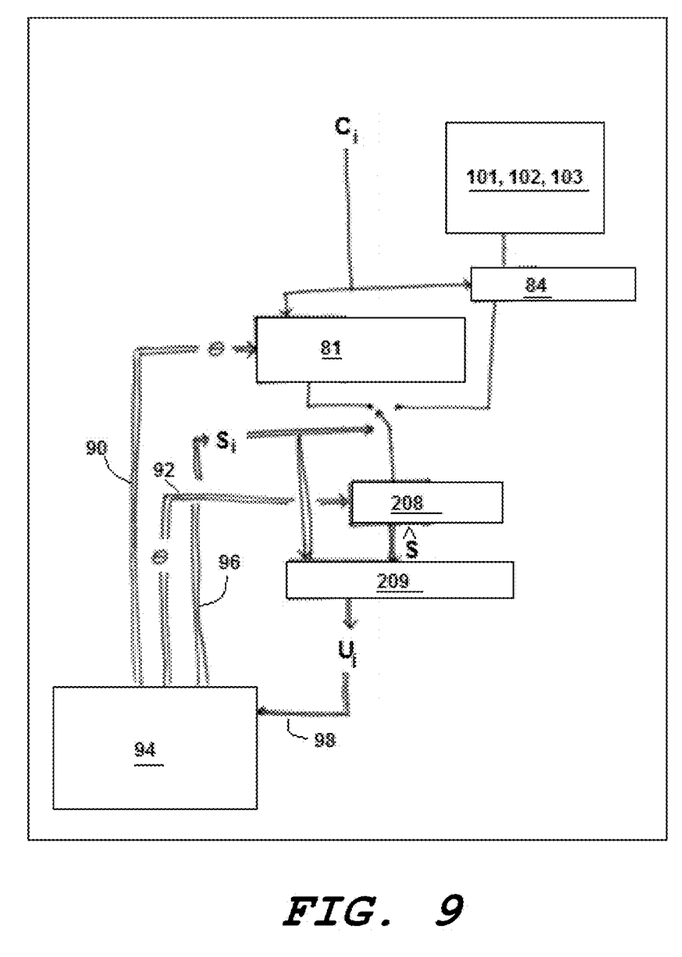
FIG. 9 shows a data flow representation of a training phase for a generalized adversarial network.

FIG. 9 shows the runtime image generator 81 being trained in the context of a generalized adversarial network. The lesion generator 81 and the discriminator 208 both receive first and second sets of weights 90, 92 from a training controller 94. These weights 90, 92 are updated as part of the training process. The discriminator 208 attempts receives either a real image or a fake image based on a selection signal 96 provided by the training controller 94. The discriminator 208 provides its educated guess to the cost function 209, which then provides, to the training controller 94, a score 98 that indicates whether the discriminator 208 was correct. This can then be used as a basis for updating the weights 90, 92.

Figure 10:
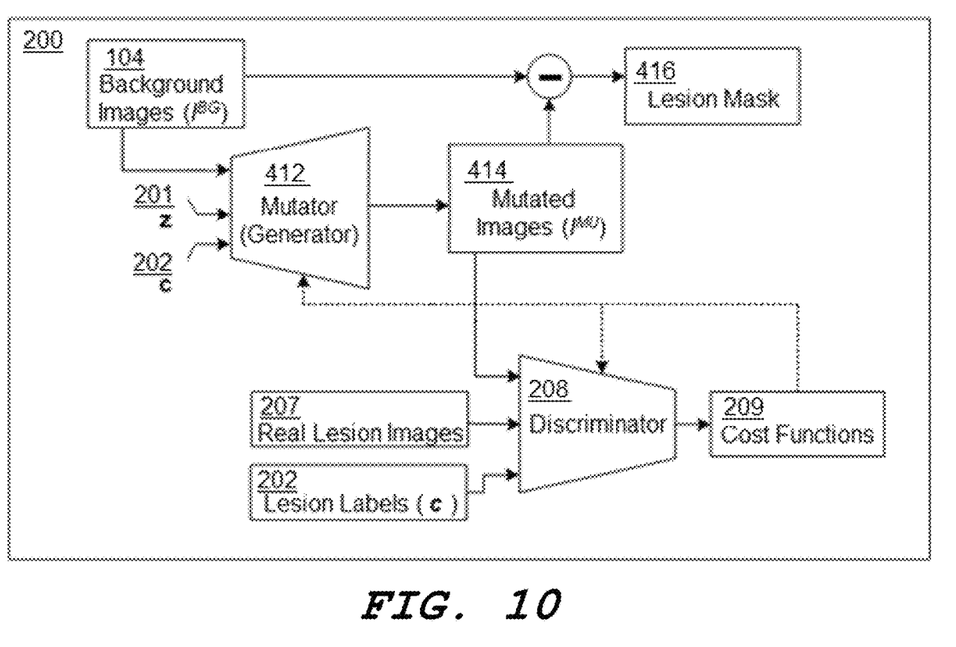
FIG. 10 shows a block diagram of an alternative lesion processor similar to that shown in FIG. 2 but modified to directly mutate a background image.

FIG. 10 shows an alternative method lesion processor 200 for carrying out synthetic image generation using a conditional generative adversarial network. The alternative lesion processor 200 method replaces both of the generation and localization steps with a mutator 412 that directly generate the faked entire lesion-fill image 414.

Like the lesion generator 203, the mutator 412 receives the noise vector 201 and the label vector 202. However, in contrast to the lesion generator 203 of FIG. 2, the mutator 412 receives the background 104 directly. The mutator 412 mutates the normal images from the background 104 directly using convolution and transposed convolutions in the layers of a neural network. This results in a set of mutated images 414. A lesion mask 416 is then derived from the difference between the mutated images 414 and the corresponding normal images 104.

By allowing the lesion to be generated with access to the normal images 104, the alternative lesion processor 200 generates a lesion that is more appropriate for the background 104. This avoids having to fit a randomly-generated lesion to the background 104.

Figure 11:
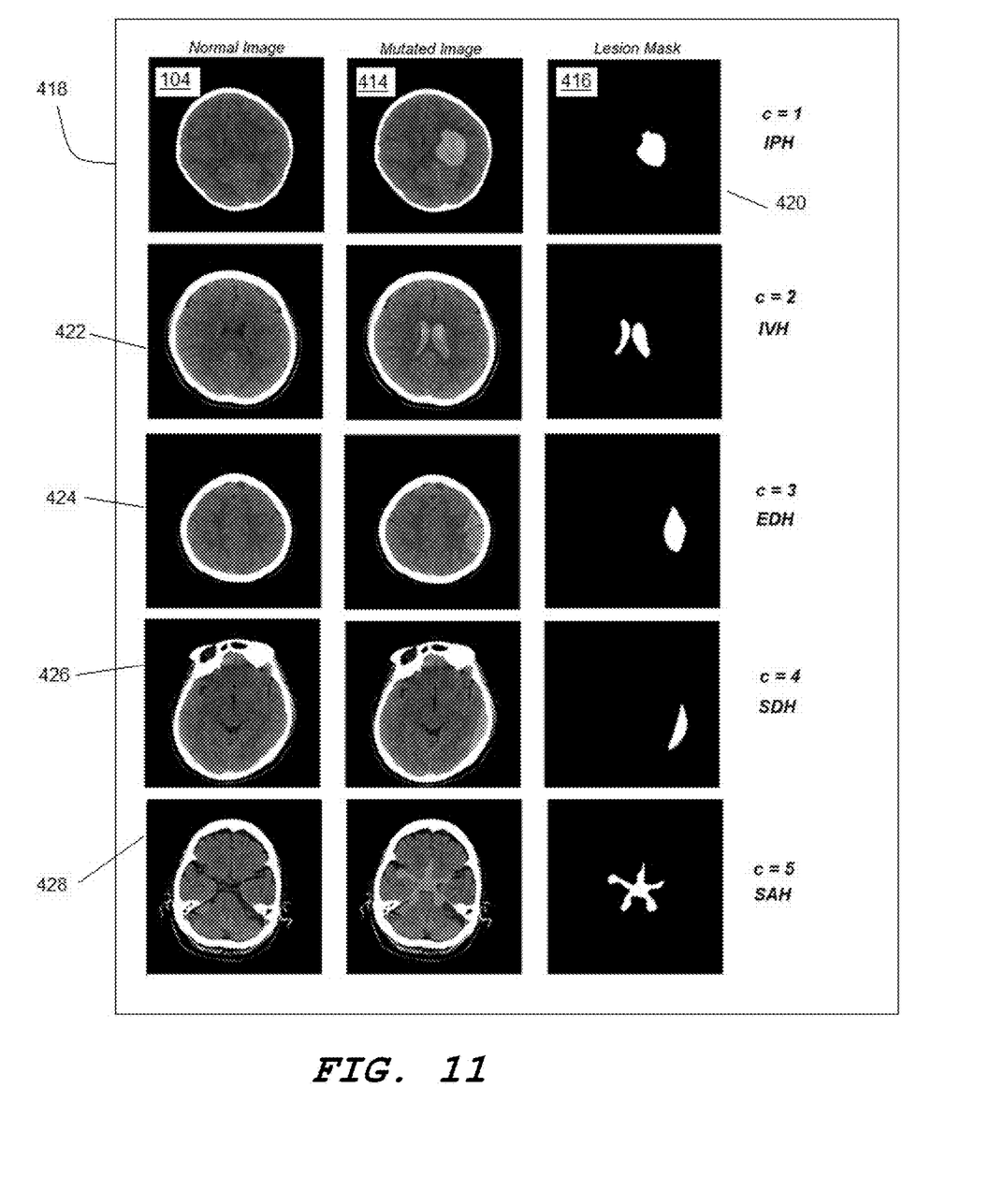
FIG. 11 shows mutated images that result from operation of the lesion processor in FIG. 10 on normal images and the corresponding lesion masks that result from such operation.

FIG. 11 shows an array 418 of images that illustrate the distinction between the background image 104, a mutated image 414, and a lesion mask 416 for several values of the label vector 202 corresponding to different types of lesion. Each row of the array 418 corresponds to a particular type of lesion. For example, the first row 420 shows an intra-parenchymal hemorrhage (IPH), the second row 422 shows an intraventricular hemorrhage (IVH), the third row 424 shown an epidural hematoma (EDH), the fourth row 426 shows a subdural hematoma (SDH), and the fifth row 428 shows a subarachnoid hemorrhage (SAH).

The mutated image 414 is similar to the background image 104 but with a region having been altered to appear like a lesion. The morphology of the lesion is a function of the label vector 202 and the noise vector 201. The corresponding lesion mask 414 corresponds to a binarization of a difference between the mutated image 414 and the background image 104.

The system 100 can thus be implemented to carry out conditional generation of data in two separate and distinct ways.

In one embodiment, the system 100 forms a semi-synthetic image by first generating a synthetic lesion and using spatial transformation to merge that synthetic lesion with a normal image. In this first embodiment, a lesion segmented image is generated using generative adversarial networks trained from patients who have abnormalities, such as hemorrhages and brain tumors. The generated lesion image is then localized by spatial transformer networks. The lesion containing images are then collected to steer the normal image transformation process.

In another embodiment, the system 100 generates the synthetic image by mutating a normal image. In either case, the result is to augment existing data by altering only certain parts of a normal image to show the lesion. This second method includes modifying the entire background image, which represents normal patients, by generating a lesion on it. Since the normal images are selected from a large population group with different ages, sex, and races or ethnicities, the generated image is highly realistic.

A convolutional neural network implements a discriminator to determine whether the final lesion-filled image appears sufficiently real. Conditions provided to the general adversarial network as conditions during the training procedure provide additional information that can be used to generate synthetic images that conform to a particular condition. Normal images are far more abundant than abnormal images. Hence, using real image texture during both of the foregoing implementations makes the final semi-synthetic more realistic and easier to generate.

Having described the invention and a preferred embodiment thereof, what is claimed as new and secured by Letters Patent is:

1. A method for generating a synthesized medical image, said method comprising receiving a normal image, generating first data based on a random selection, generating second data, and modifying said normal image to form said synthesized medical image, wherein modifying said normal image comprises combining said first data and said second data, wherein said first data characterizes an image that represents a lesion, wherein said second data characterizes a transformation of said image, and wherein said second data characterizes at least a location of said lesion, the method further comprising generating a template image and carrying out a spatial normalization process based on said template image, wherein carrying out said spatial normalization process comprises deforming a source image based on a deformation generated by a neural network, thereby generating a warped image, and determining a similarity between said warped image and said template image, wherein said neural network comprises an encoder network in communication with a decoder network, wherein said encoder network receives said source image and said template image, and wherein said decoder network generates said deformation based on data provided by said encoder network, wherein said template is created from images from a plurality of subjects.

2. The method of claim 1, wherein generating said first data comprises generating a base lesion image and wherein said second data represents a sampling of said base lesion image for forming said transformation.

3. The method of claim 2, wherein modifying said normal image comprises combining image values and locations of said normal image with corresponding image values from said transformation of said image.

4. The method of claim 1, wherein generating said first data and said second data comprise applying at least one computer-implemented non-linear transformation to a randomly-generated quantity, wherein said non-linear transformation is parameterized by first parameters.

5. The method of claim 4, further comprising using a computer-implemented training controller to determine values for said first parameters and values for second parameters of a parametrized discriminator that distinguishes between synthesized images and real lesion-containing images, providing a plurality of real lesion-containing images and a plurality of synthesized images to said parameterized discriminator, selecting values of said first parameters to reduce an aggregate measure of discriminability between real lesion-containing images and synthesized images, and selecting values of said second parameters that increase said discriminability, wherein said second parameters are parameters of a parameterized discriminator for distinguishing synthesized images and real lesion-containing images.

6. The method of claim 1, wherein said lesion is a brain lesion.

7. The method of claim 1, wherein said lesion is a lung lesion.

8. The method of claim 1, wherein modifying said normal image to form said synthesized medical image comprises directly altering image values of said normal image to synthesize a mutated image.

9. The method of claim 8, further comprising reducing an aggregate measure of discriminability between said mutated image and real lesion-containing images.

10. The method of claim 1, wherein determining said similarity comprises determining a cross-correlation between said warped image and said template image.

11. The method of claim 1, further comprising selecting said encoder network to comprise a standard form, an inception module, and a residual block.

12. The method of claim 1, further comprising generating a template image and carrying out a spatial normalization process based on said template image.

13. The method of claim 12, further comprising creating said template from images from a plurality of subjects.

14. The method of claim 1, further comprising using an encoder-decoder network training controller to determine parameter values of a transformer for anatomical normalization and selecting said parameter values to increase a similarity measure between a warped image and a source image.

15. The method of claim 1, further comprising generating said lesion by providing a lesion generator with a noise vector that represents random noise.

16. The method of claim 1, wherein said lesion is a fake lesion.

17. A method for generating a synthesized medical image, said method comprising receiving a normal image, generating first data based on a random selection, generating second data, and modifying said normal image to form said synthesized medical image, wherein modifying said normal image comprises combining said first data and said second data, wherein said first data characterizes an image that represents a lesion, wherein said second data characterizes a transformation of said image, and wherein said second data characterizes at least a location of said lesion, the method further comprising delineating said lesion based on a statistical voxel comparison between an image showing said abnormal lesion and an anatomical normalization obtained as a result of having received a demographic-specific template that has been created by averaging normalized images obtained from a population of healthy subjects that are within a designated demographic group.

18. A method for generating a synthesized medical image, said method comprising receiving a normal image, generating first data based on a random selection, generating second data, and modifying said normal image to form said synthesized medical image, wherein modifying said normal image comprises combining said first data and said second data, wherein said first data characterizes an image that represents a lesion, wherein said second data characterizes a transformation of said image, and wherein said second data characterizes at least a location of said lesion, wherein said synthesized medical image is a semi-synthetic image that comprises a combination of a background and a foreground, wherein said foreground, which comprises said lesion, is synthetic, and wherein said background is non-synthetic.

* * * * *